United States Patent [19]

Seagren

[11] Patent Number: 5,766,935
[45] Date of Patent: Jun. 16, 1998

[54] APPARATUS FOR COMPOSTING ORGANIC WASTE

[76] Inventor: Eric Seagren, 351 Tollhouse La., Fairfield, Conn. 06430

[21] Appl. No.: 634,778

[22] Filed: Apr. 19, 1996

[51] Int. Cl.$^6$ .................................................. C12M 3/00
[52] U.S. Cl. .............................. 435/290.2; 435/290.4
[58] Field of Search .............................. 435/290.1, 290.2, 435/290.4

[56] References Cited

U.S. PATENT DOCUMENTS

| | | | |
|---|---|---|---|
| 5,244,804 | 9/1993 | Horkan et al. | 435/299 |
| 5,292,637 | 3/1994 | Böhnensieker | 435/3 |
| 5,559,033 | 9/1996 | Young | 435/290.3 |
| 5,587,320 | 12/1996 | Shindo et al. | 435/290.1 |

*Primary Examiner*—David A. Redding
*Attorney, Agent, or Firm*—Fattibene and Fattibene; Arthur T. Fattibene; Paul A. Fattibene

[57] ABSTRACT

This disclosure is directed to a method and apparatus for recycling organic waste material into reusable compost. This is attained by shredding or grinding organic waste and mixing the ground waste into a homogeneous mass and conveying the homogeneous mass to a decomposition chamber where it is aerated with recirculating air to decompose into a reusable compost. The apparatus for carrying out the process includes a compact, self-contained housing having a component section and a decomposition chamber. The waste material is ground and mixed in the component section and then conveyed to the decomposition chamber by a conveyor which disperses the homogenous waste longitudinally and laterally within the decomposition chamber. A blower directs aerating air into the decomposition chamber and the air is recirculated back to the blower, where the recirculated air is mixed with a predetermined amount of incoming fresh air, and a portion of the recirculating air is exhausted to atmosphere, the exhausting air being filtered prior to being exhausted. Thereafter, the resulting compost is removed by an auger through a discharge opening of the decomposition chamber.

13 Claims, 5 Drawing Sheets

5,766,935

APPARATUS FOR COMPOSTING ORGANIC WASTE

FIELD OF THE INVENTION

This invention relates to a method and apparatus for composting organic waste, and more specifically to a method and apparatus for recycling and/or converting waste organic products into usable compost on site.

PROBLEM AND PRIOR ART

Heretofore, the accumulation of waste products at various types of food establishments, e.g. grocery stores, supermarkets, large restaurants, wholesale fruit and vegetable packers, food distributors and the like, had resulted in a considerable waste disposal problem. Such waste consists primarily of spoiled fruits, vegetables and the crates and cartons in which such products are shipped. Generally, the crates and cartons, which are generally formed of wood or cardboard, had to be segregated from the spoiled fruits and vegetables and treated separately for disposal purposes. In addition, the accumulations of such waste had to be separately carted in dumpsters to various land fills or other suitable disposable areas, e.g. incinerators or the like. As landfills are being phased out in many regions, and incineration constitutes a source of air pollution, the problem of the disposing of such waste material is ever-increasing and rendering it ever more expensive for such establishments to dispose of their waste material.

As a result of this ever-increasing problem, numerous attempts have been made in an effort to solve this growing disposal problem. Some of these known efforts are disclosed in U.S. Pat. Nos. 3,721,183; 4,830,188; 5,101,977; 5,165,612; 5,377,921 and 5,425,507. Generally, such known efforts have resulted in relatively complex and costly apparatuses and/or methods for treating only certain types of waste, e.g. rubbish processed into various predetermined shapes, plastic fragments, municipal solid waste (MSW), organic wastes, metals, glasses and the like. Each such known system has its specific use and/or limitations, and/or requires relatively complex and costly apparatuses.

SUMMARY OF THE INVENTION

This invention is directed to a method and apparatus for disposing organic waste, e.g. rotten or wasted fruits and vegetables and the cardboard containers in which such produce are shipped to various grocery outlets, supermarkets, restaurants and the like. Basically, the apparatuses include an outer shell or housing for housing the component parts. Essentially, the housing includes a component section and a connected decomposition chamber. Disposed within the component section is a hopper or chute for directing the waste material, which may comprise a mixture of cardboard cartons and the spoiled organic matter such as fruits and vegetables, to a grinder where such waste material is shredded or ground. A mixer is disposed adjacent the outlet of the grinder to blend the cardboard and organic waste into a homogeneous mixture. From the mixer, the homogeneous mixture is directed to the decomposition chamber by a conveyor. A conveyor extending along the top of the decomposition chamber is provided to uniformly disperse the mixture of organic waste and cardboard uniformly along the length of the decomposition chamber in which the mixture is treated and aerated by air emanating from an air supply manifold extending longitudinally of the decomposition chamber. Disposed adjacent the roof or top of the decomposition chamber are air return conduits for recycling the air to the blower disposed in the component chamber where the recirculating air is mixed with a predetermined amount of incoming fresh air.

Connected to the outlet of the blower is a Y connection that is valved by proportional dampers for directing a predetermined amount of air to the aerating conduit, and exhausting the remainder air to an exhaust outlet. In accordance with this invention, the conduit directing the remainder air to the exhaust outlet may be filled with a suitable filtering material, e.g. cardboard or a bio-filter material which may comprise the compost or end product produced in the decomposition chamber. The placement of such filter material in the conduit directing the recirculated air to the exhaust outlet functions to minimize any disagreeable odor being vented to the atmosphere.

A conveyor is disposed along the bottom of the decomposition chamber for moving the final compost to a discharge outlet where it can be collected and trucked away or bagged for subsequent resale as compost or fertilizer. If desired, a spray may be provided within the decomposition chamber for introducing a predetermined amount of moisture into the chamber to aid in the decomposition of the waste material.

An object of this invention is to provide for a compact, self-contained unit that is relatively simple in construction, and positive in operation.

Another object is to provide a method and apparatus for composting a mixture of waste cardboard and organic matter to form a reusable compost material.

Another object is to provide an on-site composting apparatus for converting waste cardboard and spoiled fruits or vegetables into reusable compost on site.

Another object is to provide a process whereby the volume of waste can be drastically reduced by speeding up the decomposition cycle and recycling the resulting end product as reusable compost.

Other features and advantages will become more readily apparent when considered in view of the drawings and following description in which.

DETAILED DESCRIPTION

Figure 1:
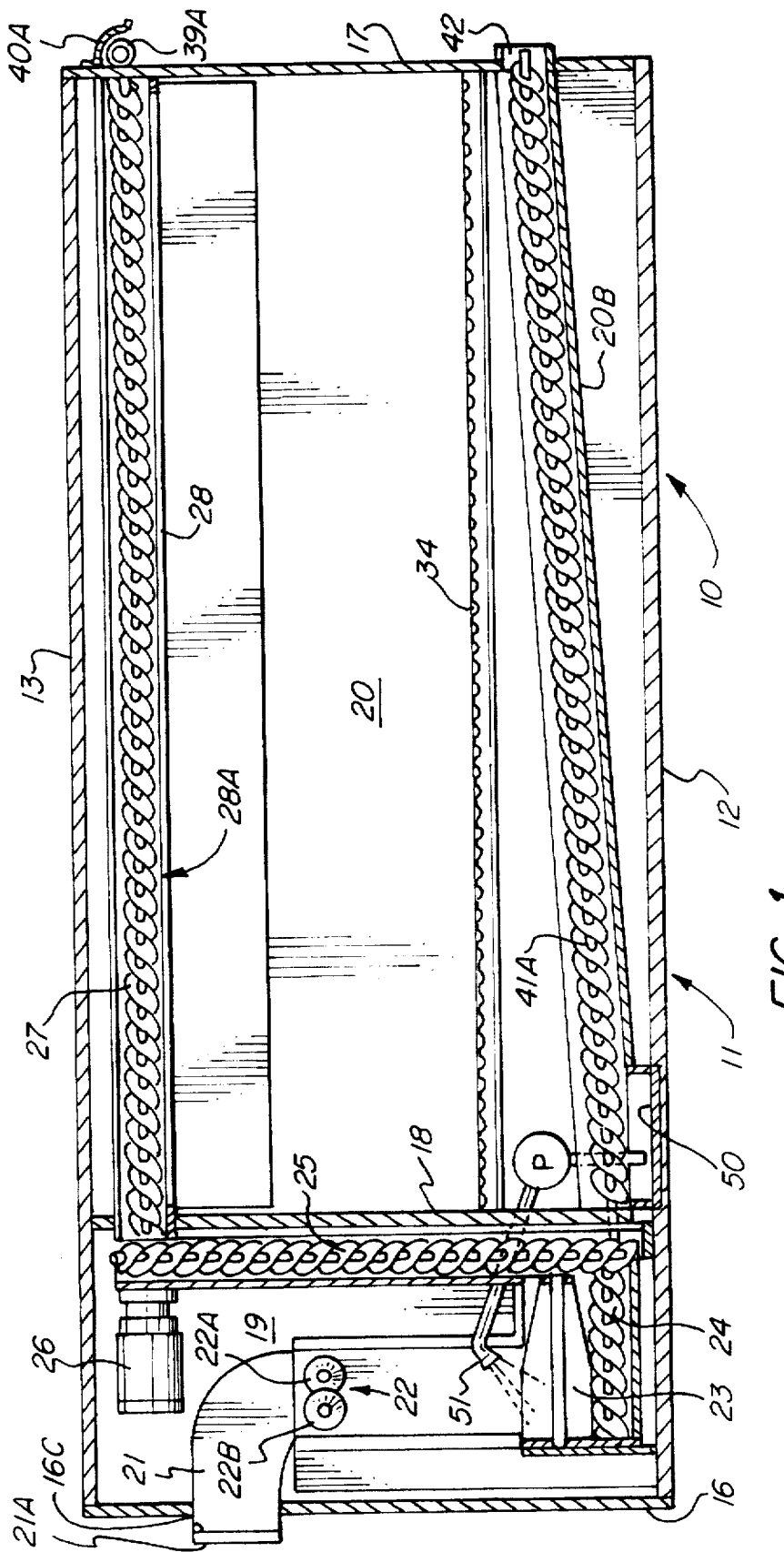
FIG. 1 is a sectional side elevation view of an embodiment of this invention.

Referring to the drawings, there is illustrated in FIGS. 1 to 6 an embodiment of the present invention. As shown, the onsite composting apparatus 10 comprises an outer shell or housing 11 having opposed side walls 12 and 13 with connected top and bottom walls 14 and 15, respectively, and enclosed by end walls 16 and 17 to define an enclosure or box-like container. It will be understood that the housing 11 is formed of suitable weatherproof materials as e.g. sheet metal, wood or any other structural building material. The illustrated housing 11 is approximately 8 feet by 8 feet by 20 feet, whereby it can be rendered readily portable. However, it will be understood that the respective dimensions are not critical, and the housing can be variously sized depending upon the desired capacity of the unit. As it will be hereinafter noted, the principle components are housed within housing 11 so that it can be placed on site where it is to be used or needed.

As best seen in FIG. 1, the housing 11 is internally divided by a partition or wall 18 to define a component section 19 and a composting chamber 20. The end wall 16 may be defined by two door panels 16A, 16B which are suitably hinged to swing between open and closed position so as to provide ready access to the component section 19.

Figure 2:
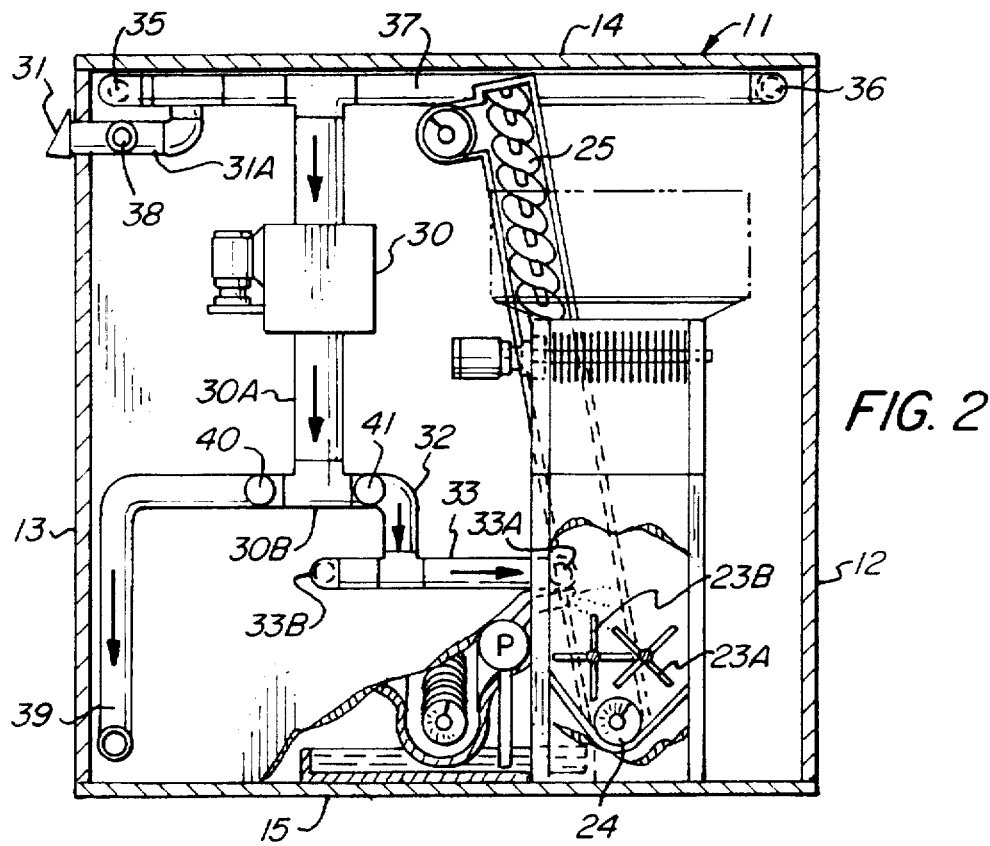
FIG. 2 is a sectional left end view of FIG. 1.
Figure 4:
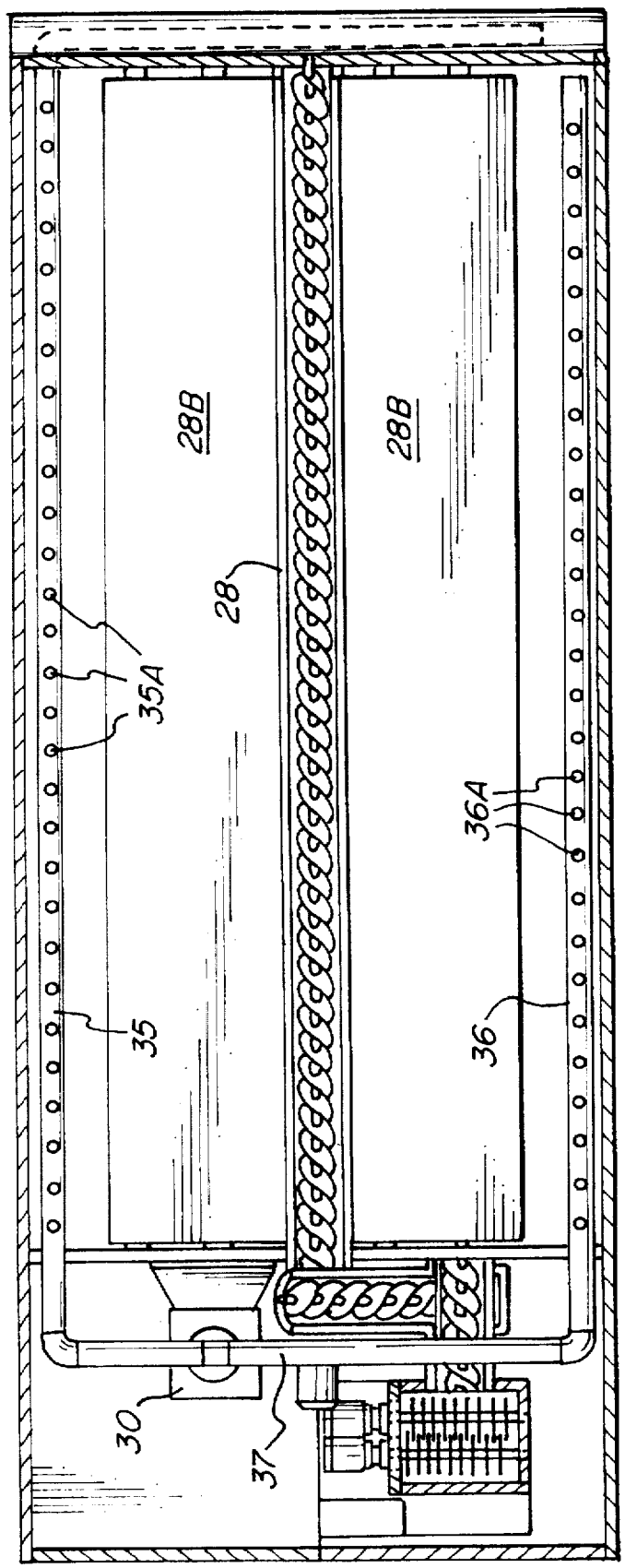
FIG. 4 is a sectional top or plan view of FIG. 1.
Figure 5:
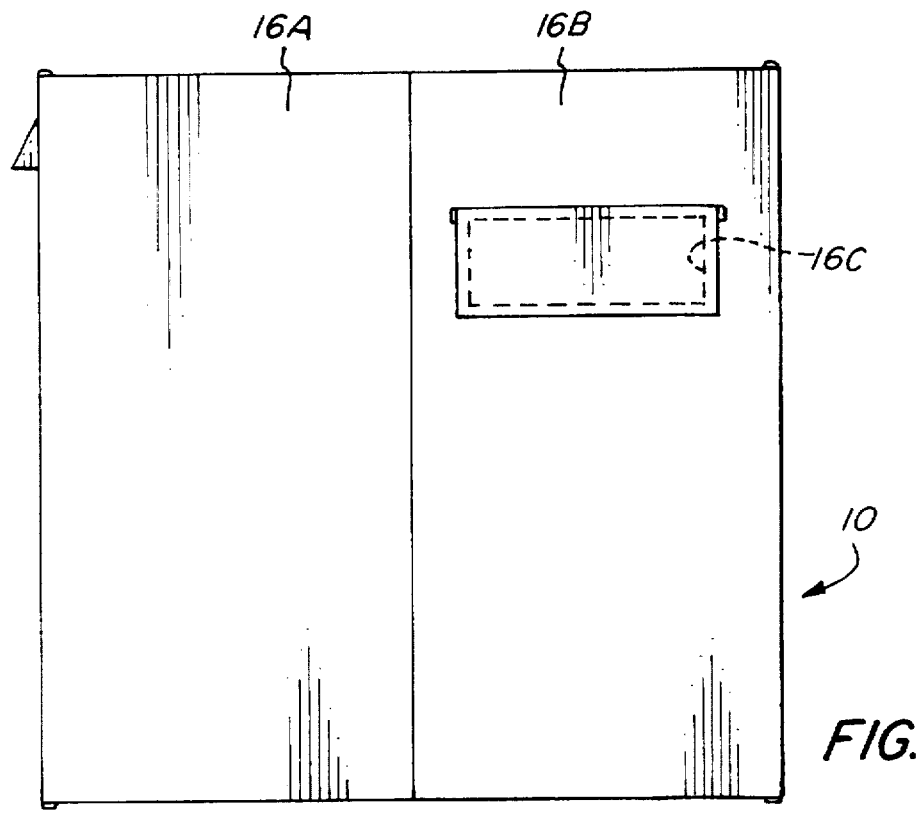
FIG. 5 is a left end view of FIG. 4.
Figure 6:
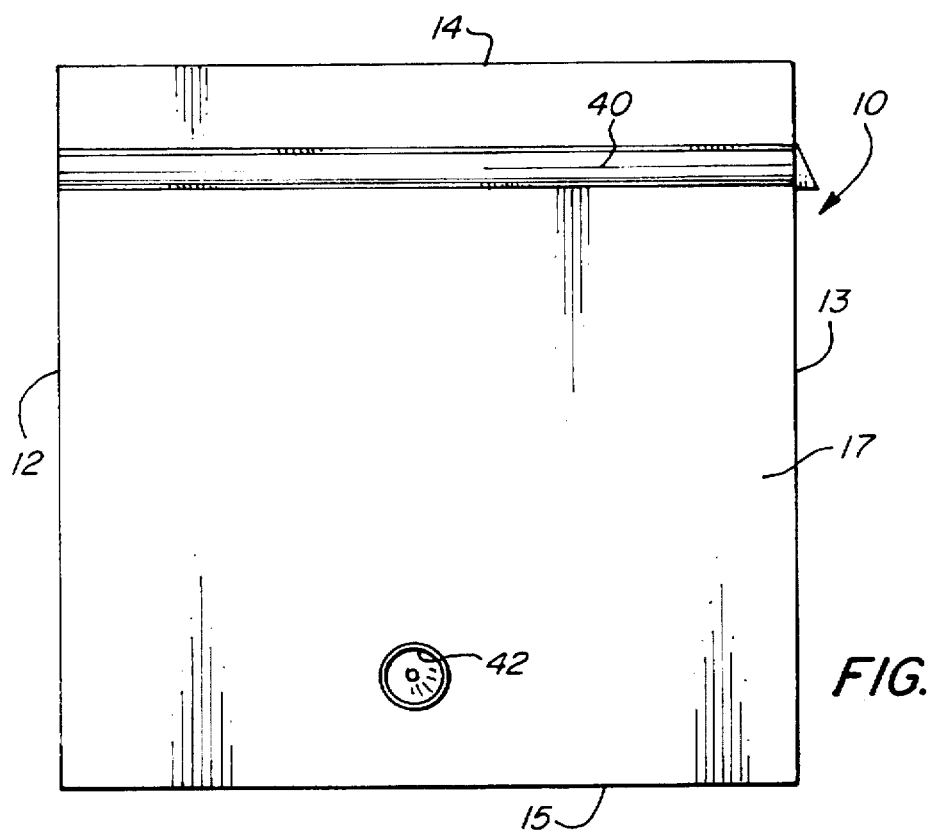
FIG. 6 is a right end view of FIG. 4.

As best seen in FIGS. 1 and 5, the side door panel 16B is provided with an opening 16C for receiving the inlet 21A of a chute or hopper 21 into which the organic waste, such as fruits, vegetables, cartons and the like to be disposed or recycled are placed. Adjacent the outlet or bottom of the chute or hopper 21 is a grinder or shredder 22 for grinding or shredding the waste material. As best seen in FIGS. 1 and 4, the grinder or shredder comprises a series of counter-rotating cutting blades 22A, 22B, through which the waste material passes. The grinding or shredding of the waste material into greatly reduced size facilitates the decomposition thereof, as will be herein described. Disposed adjacent the discharge end of the grinder or shredder is a mixer 23 which blends or mixes the various types of waste material to form a generally homogeneous mixture of waste material. As seen in FIG. 2, the mixer 23 may comprise counter rotating paddle wheels 23A, 23B.

Disposed below the mixer 23 is a conveyor, e.g. a screw conveyor or auger 24 for advancing the homogeneous mixture of waste toward a second or vertical conveyor 25. In the illustrated embodiment, the vertical conveyor 25 comprises a screw or auger for lifting the homogeneous mixture to the upper portion of the component section 19.

At the upper end of the component section is a suitable driving means, e.g. an electric motor 26 for driving an elongated conveying means illustrated in the form of a horizontal screw conveyor 27 for uniformly dispersing the homogeneous mixture along the length of the decomposition chamber 20. In accordance with this invention, the horizontal dispersing conveyor 27 is disposed within a trough 28 that extends along the upper end of the decomposition chamber 20. As shown, the trough 28 is provided with longitudinally extending trough openings 28A. It will be noted that as the conveyor or auger 27 is actuated, the homogeneous mass of waste being advanced along the trough will pass through the openings 28A so that the waste can be uniformly dispersed along the length of the decomposition chamber 20. Connected to the under surface of the trough 28 are a plurality of radially spaced baffles 28B for dispersing the waste material laterally of the decomposition chamber. Uniformly distributing the shredded homogeneous waste material, both longitudinally and laterally of the decomposition chamber, enhances the uniform rate of decomposition.

Figure 3:
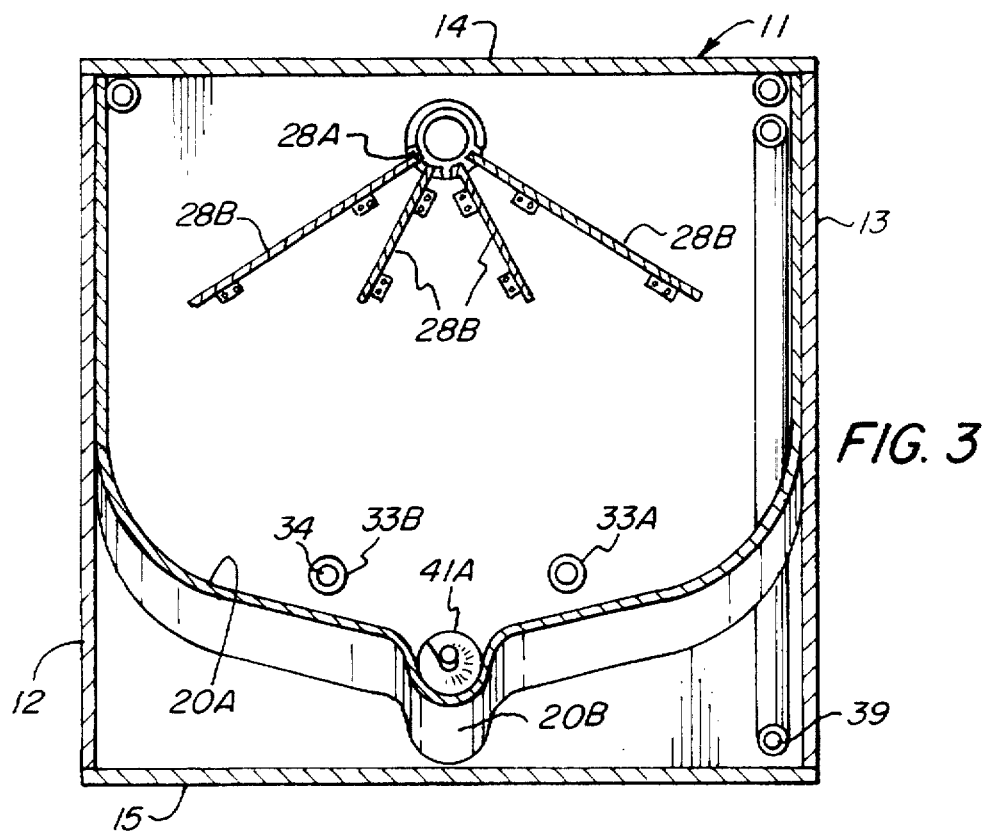
FIG. 3 is a sectional right end view of FIG. 1.

To aid in the decomposition of the homogeneous mixture being dispersed within the decomposition chamber 20 is a means for introducing air for aerating the waste mixture as it is being dispersed. The aerating means comprises an air blower 30 which is connected into communication with a suitable fresh air inlet 31. The outlet 30A of the blower 30 is connected to a conduit 32 which is connected into communication with a U shaped aerating conduit 33 having its parallel side arms 33A, 33B extending horizontally of the decomposition chamber 20 at a location spaced above the bottom 20A of the decomposition chamber 20. As shown in FIG. 3, the bottom 20A of the decomposition chamber 20 slopes toward a centrally disposed and longitudinally extending well portion 20B. The well portion, as shown in FIG. 1, is sloped downwardly to the left so as to drain any excess moisture toward a drain pan or collector 50. If desired, the internal surface of the decomposition chamber may be coated with an anti-stick material such as Teflon so as to prevent any of the waste from sticking thereto, and to facilitate the gravitation of the waste toward the well portion 20B which forms the lowermost portion of the decomposition chamber 20.

The parallel side arms 33A, 33B of the aerating conduit 33 are perforated with a series of openings 34 through which aerating air is introduced into the decomposition chamber. In operation, the aerating air discharging through the perforations 34 of conduit 33 aerates the homogeneous waste material being dispersed longitudinally and laterally of the decomposition chamber to convert the waste material over a period of time into reusable compost.

A means is provided for recirculating the aerating air being introduced into the decomposition chamber 20 back to the negative side of the blower 30 for recirculation to the decomposition chamber. This is attained by providing opposed air recirculation conduits 35, 36 which are perforated or provided with openings 35A, 36A respectively. Conduits 35 and 36 connect into communication with an interconnecting branch 37 for re-directing the recirculating air back to the negative side of the blower 30. As best seen in FIG. 2, the air inlet 31 connects into the recirculation branch 37 by conduit 31A, whereby the incoming fresh air is mixed with the recirculating air being redirected to the blower 30. To proportion or control the amount of incoming fresh air, a control valve or proportioning damper 38 is disposed in conduit 31A.

Connected to the outlet 30A of the blower 30 is a tee connection 30B. One end of the tee connection 30B is connected in communication to the aerating conduit 33 and the other end of the tee connection 30B is connected into communication with an exhaust conduit 39 which exhausts to the atmosphere at 39A. As best seen in FIG. 2, proportioning dampers 40 and 41 are disposed at opposed ends of the tee connection 30B so as to control or proportion the amount of air being directed to the aerating conduit 33 and the exhaust conduit. The exhaust conduit 39 extends along the bottom of the housing 11 and then upwardly along the rear and thence horizontally along the upper end of the side wall 17 exteriorly thereof as at 39A. A shield or cover 40A is provided to protect the exposed portion of the external exhaust conduit 39A.

In accordance with this invention, the exhaust conduit 39 may be filled with a suitable filtering material, e.g. charcoal or with a bio-filtering material, e.g. the residue compost for minimizing the odor of the exhausting air or gases to atmosphere.

Disposed in the well 20B of the decomposition chamber is a discharging conveyor in the form of a screw or auger 41A for advancing the reusable residue or compost to a discharge opening 42 where the compost can be collected or bagged into suitable containers.

From the foregoing, it will be readily apparent that a wholly contained unit for recycling organic waste into reusable compost can be placed on site of those establishments which have a need of disposing of excess organic waste such as rotten fruits, vegetables, and cartons. Such establishments having a particular need for the apparatus described are supermarkets, wholesalers of fruits and vegetables, groceries or other establishments charged with disposing of organic waste materials.

In the event the organic waste to be disposed has a high liquid content, e.g. melons and the like, a means may be provided for extracting the liquid or juices and separating such liquid or juices from the solid pulp or waste, and thereafter recirculating the separated juice or liquid to the decomposing chamber 20. As an optional equipment, a perforated separation plate may be disposed adjacent the discharge end of the shredder, which is disposed at an inclined angle. The juices, extracted from the waste as it is being ground or shredded, pass through the perforations of the inclined separator and collected as the solid waste sliding off the separator plate and guided into the mixer for blending. The liquid of the juices extracted from the solid waste passing through the openings formed in the separator plate is collected and directed to a suitable liquid collector 50. The collected juices are then pumped to a suitable spray means 51 disposed in the decomposition chamber whereby the liquid is sprayed onto the homogeneous waste being blended to aid in the decomposition of the solid waste. In operation, the solid waste such as rotten fruits, vegetables, cardboard and the like is introduced into the chute 21 where it is directed to the grinder 22, where it is shredded as described. The shredded waste is then directed to the blender or mixer to form a homogeneous mixture and where moisture may be added as needed. The homogeneous mixture is then conveyed and raised to the top of the decomposition chamber where it is transferred to a dispersing conveyor 27 where the homogeneous mixture is uniformly dispersed in both a longitudinal and lateral direction as the waste free-falls into the decomposition chamber 20. Intermixing with the free falling waste is a stream of aerating air which is recirculated by means of a recirculating blower 30. The recirculating air is tempered by fresh incoming air so that fresh air, mixed with a portion of the recirculating air, is recirculated back to the decomposition chamber 20. Also, a portion of the mixed fresh and recirculating air is exhausted to atmosphere, whereby the amount of exhausting air substantially equals the amount of fresh air introduced into the cycle. In exhausting, the exhausting air is filtered to minimize the odor or undesirable gases being exhausted. In time, the solid waste fruits, vegetables, cartons and the like will decompose into a reusable and recyclable compost.

Figure 7:
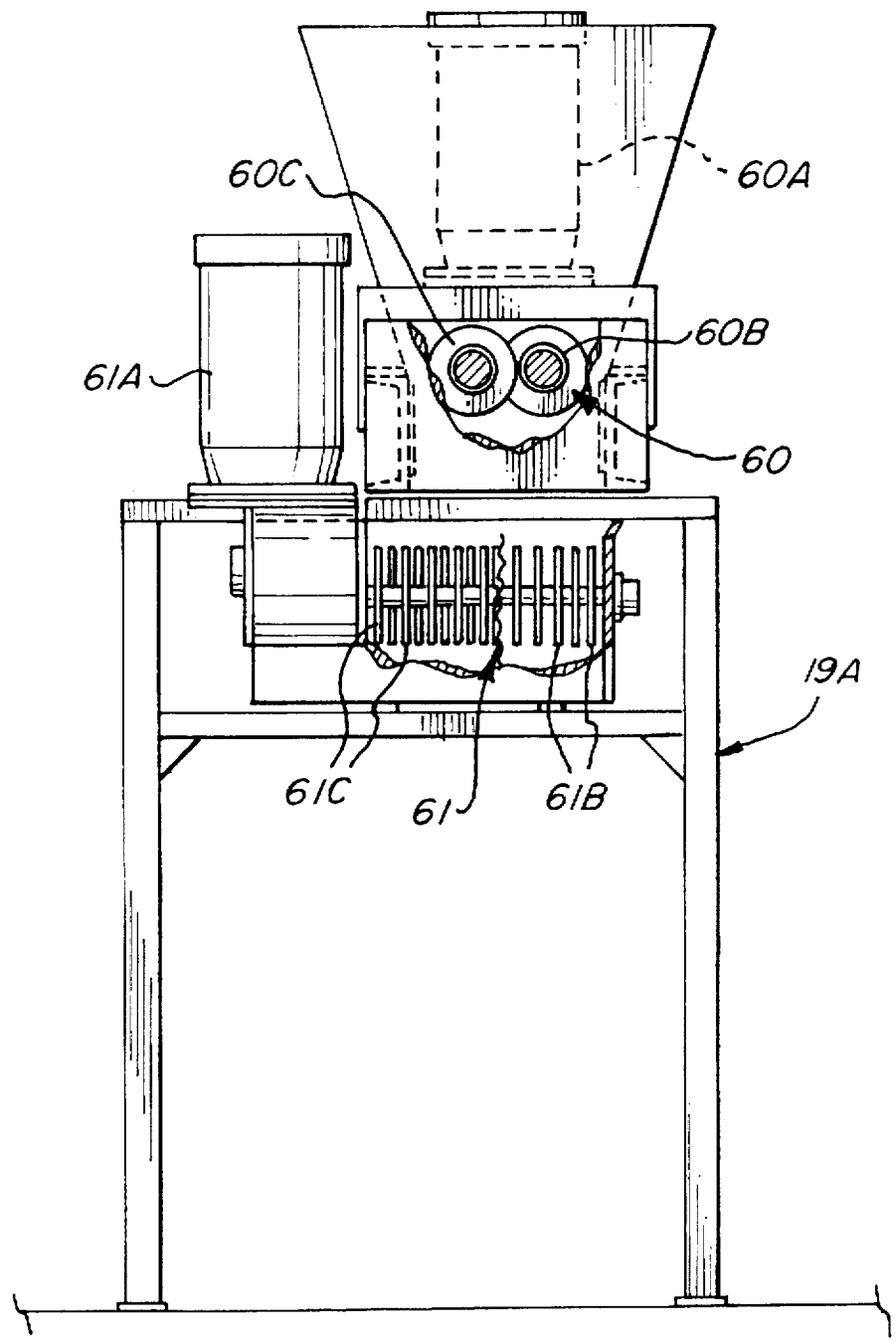
FIG. 7 is an end view of a modified form of the invention.

FIG. 7 illustrates a slightly modified form of the invention. In this form, the component section 19A is provided with two sets of grinders or shredders 60 and 61, each of which is independently driven by drive motors 60A and 61A respectively. Each set 60, 61 of grinders or shredders includes a series of opposed counter rotating cutting blades 60B, 60C and 61B, 61C respectively. As best seen in FIG. 7, the respective grinders or shredders 60 and 61 are disposed in vertically spaced relationship. The upper shredder 60 has its axis disposed normal to the axis of the lower shredder 61. Thus, in operation, the raw waste, in passing through the upper shredder 60, is shredded into a particular particle size and then directed through the lower shredder 61 where it can be shredded into a finer particle size. It will be understood that the spacing and number of blades of the respective shredders determine the fineness or degree of shredding desired. In all other respects, the composting apparatus is as hereinbefore described.

While the present invention has been described with respect to a particular embodiment, various modifications may be made without departing from the spirit or scope of the invention.

What is claimed is:

1. A self contained apparatus for converting a mixture of organic waste generated by grocery stores, supermarkets, large restaurants, wholesale fruit and vegetable packers, and food distributors into reusable compost comprising a stationary housing partitioned to define a component section and an elongated decomposition chamber, said decomposition chamber having a chamber inlet adjacent one end thereof, a chute disposed in said component section, said chute having an inlet and an outlet, a grinder disposed adjacent the outlet of said chute for grinding the organic waste introduced into said chute, a mixer downstreamwise from said grinder for receiving the ground organic waste and blending said organic ground mixture waste into a homogeneous mixture, conveying means for conveying said homogeneous mixture from said mixer to said decomposition chamber inlet, a second conveyor means for conveying said homogeneous mixture from said chamber inlet longitudinally along the length of said decomposing chamber, dispersing means adjacent said said second conveying means for receiving and dispersing said homogeneous mixture in a uniform manner along the length of said decomposition chamber, air supply means for introducing controlled air into said decomposition chamber to aid in the decomposition of said ground waste material in said decomposition chamber, means for recirculating the gases formed in the decomposition chamber to said air supply means, said decomposition chamber having a discharge opening, and a third conveyor means extending along the bottom of said decomposition chamber for directing the decomposed waste to said discharge opening.

2. A self-contained apparatus for converting a mixture of organic waste into reusable compost as defined in claim 1 wherein said means for introducing air into said decomposition chamber comprises:

an aerating conduit extending longitudinally of said decomposition chamber, said aerating conduit having a series of perforations spaced along the length thereof, and a blower disposed in said component section, said blower having an outlet connected in communication with said aerating conduit, and an air inlet connected to said blower through which fresh air is supplied to said blower.

3. A self-contained apparatus for converting a mixture of organic waste into reusable compost as defined in claim 2 and including:

means for recirculating the air introduced into said decomposition chamber, said recirculation means including a return air tube extending along the top of the decomposition chamber, said return air tube having a series of openings spaced longitudinally thereof, and said return air tube being connected in communication with the inlet to said blower whereby said recirculated air is mixed with incoming fresh air.

4. A self-contained apparatus for converting a mixture of organic waste into reusable compost as defined in claim 3 and including:

a balancing valve in said air inlet for controlling the amount of fresh air directed to said blower.

5. A self-contained apparatus for converting a mixture of organic waste into reusable compost as defined in claim 3 and including means for exhausting a predetermined amount of said recirculated air, said exhaust means comprising an exhaust conduit connected in communication to the outlet of said blower, and proportioning dampers disposed in said exhaust conduit and aerating conduit for proportioning the amount of mixed fresh and recirculated air directed to said aerating conduit and to said exhaust conduit, and said exhaust conduit having a discharge end exhausting to atmosphere.

6. A self-contained apparatus for converting a mixture of organic waste into reusable compost as defined in claim 5 and including:

a bio-filtering material disposed in said exhaust conduit filtering the exhaust air flowing therethrough to atmosphere.

7. A self-contained apparatus for converting a mixture of organic waste into reusable compost as defined in claim 1 wherein the interior surface of said decomposition chamber is coated with a non-stick material.

8. A self-contained apparatus for converting a mixture of organic waste into reusable compost as defined in claim 1 wherein said dispersing means comprises a trough extending substantially the length of said decomposition chamber, said second conveyor means being disposed in spaced relationship in said trough, said trough having a series of spaced apart openings formed therein wherein said homogeneous mixture being advanced along said trough by said second conveyor means passes through said spaced openings to uniformly disperse the homogeneous material longitudinally of said decomposition chamber.

9. A self-contained apparatus for converting a mixture of organic waste into reusable compost as defined in claim 8 and including a plurality of radially spaced longitudinally extending baffles connected to said trough for laterally dispersing said homogeneous mixture.

10. A self-contained apparatus for converting a mixture of organic waste such as fruits, vegetables and the crates and cartons in which such fruits and vegetables are shipped into reusable compost on site comprising:

a stationary housing partitioned to define a component section and a connected decomposition chamber having an inlet adjacent the upper end thereof, a chute having an inlet and an outlet disposed in said component section, a grinder adjacent said chute outlet for shredding waste material placed in said chute, a mixer disposed downstreamwise from said grinder for blending the shredded material to form a homogeneous mixture of the shredded material, a conveyor for transporting the homogeneous mixture to said decomposition chamber inlet, a dispersing conveyor means extending longitudinally of said decomposition chamber, said dispersing conveyor means including an auger extending-longitudinally along the upper portion of said decomposition chamber, a trough disposed about said auger in spaced relationship thereto, said trough having a series of longitudinally spaced openings therein through which the mixture advanced by said auger is dispersed into said decomposition chamber, a plurality of radially disposed longitudinally extending baffles connected to said trough for laterally dispersing the mixture discharged through said trough openings, aerating means for introducing air into said decomposition chamber to and through the shredded waste material in said decomposition chamber, said aerating means including a blower disposed in said component section, an aerating conduit connected to said blower extending longitudinally of said decomposition chamber, a recirculating air conduit disposed in said decomposition chamber for recirculating the gases in said decomposition chamber to said blower, an air inlet for introducing fresh air to said recirculated gases, a balancing valve for controlling the amount of fresh air introduced to said recirculating gases, an exhaust conduit for exhausting a portion of said recirculated gases to atmosphere, a filtering material disposed in said exhaust conduit for minimizing any odor present in the exhausting gases, and a discharging conveyor disposed at the bottom of said decomposition chamber for discharging the residue compost.

11. A self contained apparatus for converting a mixture of organic waste into reusable compost as defined in claim 1 wherein said grinder comprises:

a first and second set of opposed counter rotating cutting blades, said first and second set of opposed counter rotating cutting blades being vertically spaced within said component section.

12. A self contained apparatus for converting a mixture of organic waste into reusable compost as defined in claim 11, wherein the axis of said first and second set of opposed counter rotating cutting blades are disposed normal to one another.

13. A self-contained apparatus for converting a mixture of organic waste as defined in claim 10 and including a means for separating and collecting the liquid content in said waste material, and means for spraying the collected liquid content onto the shredded waste as it is being blended in the mixture to aid in the decomposition thereof.

* * * * *